(12) United States Patent
Van Dyke et al.

(10) Patent No.: US 9,339,296 B2
(45) Date of Patent: May 17, 2016

(54) JOINT DISTRACTION SYSTEM

(71) Applicant: Biomet Manufacturing, LLC, Warsaw, IN (US)

(72) Inventors: William Scott Van Dyke, Columbia City, IN (US); Mark Hutchins, York, PA (US); Richard Blackwell, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 14/309,214

(22) Filed: Jun. 19, 2014

(65) Prior Publication Data
US 2015/0366587 A1 Dec. 24, 2015

(51) Int. Cl.
*A61B 17/66* (2006.01)

(52) U.S. Cl.
CPC ...................... *A61B 17/66* (2013.01)

(58) Field of Classification Search
CPC ............ A61B 17/171; A61B 17/6416; A61B 17/6458; A61B 17/88; A61B 17/6425; A61B 17/6491; A61B 17/66; A61B 2017/00902; A61B 2017/603; A61B 2017/1782
USPC ...................... 606/53–60, 246–249
See application file for complete search history.

(56) References Cited

U.S. PATENT DOCUMENTS

| 5,620,442 | A | | 4/1997 | Bailey et al. |
| 5,931,837 | A | * | 8/1999 | Marsh et al. ............... 606/55 |
| 6,152,925 | A | * | 11/2000 | Marsh et al. ............... 606/54 |
| 6,428,540 | B1 | * | 8/2002 | Claes et al. ................ 606/53 |
| 7,261,713 | B2 | * | 8/2007 | Langmaid et al. ........... 606/59 |
| 7,832,401 | B2 | | 11/2010 | Torrie et al. |
| 7,947,006 | B2 | | 5/2011 | Torrie et al. |
| 8,187,308 | B2 | | 5/2012 | Mullaney et al. |
| 2006/0100562 | A1 | | 5/2006 | Pamplin |
| 2011/0190676 | A1 | | 8/2011 | Torrie et al. |

(Continued)

FOREIGN PATENT DOCUMENTS

| EP | 1272115 | 8/2003 |
| EP | 2152219 B1 | 6/2013 |
| WO | WO2007080454 A2 | 7/2007 |

(Continued)

OTHER PUBLICATIONS

Arthrodiatasis—Articulated Joint Distraction by Orthofix Oct. 20, 2009.

(Continued)

*Primary Examiner* — Pedro Philogene
(74) *Attorney, Agent, or Firm* — Schwegman Lundberg & Woessner, P.A.

(57) ABSTRACT

An external fixation system for adjusting a load occurring at a joint connecting a first bone to a second bone. The external fixation system includes a first bone clamp to connect to the first bone, a second bone clamp to connect to the second bone, and a pivot assembly to operatively connect the first bone clamp and to the second bone clamp. The pivot assembly includes a first pivot body pivotably coupled to a second pivot body at a pivot axis, wherein one of the first pivot body and the second pivot body includes an adjustment mechanism configured to adjust the position of one of the first pivot body and the second pivot body with respect to the other of the first pivot body and the second pivot body at other than the pivot axis.

21 Claims, 9 Drawing Sheets

(56) References Cited

U.S. PATENT DOCUMENTS

| | | |
|---|---|---|
| 2012/0203225 A1 | 8/2012 | Mingozzi et al. |
| 2012/0240938 A1 | 9/2012 | Pamichev |

FOREIGN PATENT DOCUMENTS

| | | |
|---|---|---|
| WO | WO2007080454 A2 | 7/2007 |
| WO | WO2008150731 A1 | 12/2008 |
| WO | WO2009058830 | 5/2009 |
| WO | WO2009111319 | 9/2009 |
| WO | WO2009152470 A1 | 12/2009 |
| WO | WO2012024078 A2 | 2/2012 |
| WO | WO2012064786 A1 | 5/2012 |
| WO | WO2012129097 A1 | 9/2012 |
| WO | WO2013166187 A1 | 11/2013 |

OTHER PUBLICATIONS

DFS—Hip Distractor, Surgical Technique by Biomet Jan. 1, 2001.

* cited by examiner

JOINT DISTRACTION SYSTEM

FIELD

The present disclosure relates to an orthopedic external fixation system and more particularly a joint distraction system.

BACKGROUND

In various orthopedic surgical procedures, it is often necessary to secure or stabilize: i) two or more portions of a bone or soft tissue, ii) bones connected to one another at an articulable joint, or iii) a joint itself. This necessity can result from a bone or soft tissue injury, such as an acute fracture of the bone, or from wear and tear resulting from overuse or age. To ensure that the damaged bone, soft tissue, or joint are properly healed, the damaged bone, soft tissue, or joint must be adequately stabilized during the healing process. To adequately align and stabilize the injured bone fragments and/or soft tissue, a bone distraction frame is typically installed to the patient.

Once a distraction frame has been installed onto a patient, it is sometimes necessary to further adjust the frame to fine tune the alignment of the damaged bone fragments, soft tissue, or joint. This process, referred to as "fracture reduction," is typically performed under the guidance of a C-arm (X-ray) and in which a surgeon adjusts the distraction device until the bones, soft tissue or joint is aligned to a desired orientation. Once the surgeon is satisfied, the clamps of the distraction frame can then be tightened.

Hip distraction is used to unload the stresses of the hip joint while permitting a free range of motion of the hip joint. Distraction techniques can have very specific applications and are typically performed only in cases where off-loading the joint is expected to provide a distinct advantage in patient treatment. For instance, hip distraction can be used in the treatment of: 1) avascular necrosis of the femoral head; 2) Legg-Calves-Perthes Diseases; 3) chondrolysis; 4) protection of the joint after femoral head fracture; and 5) after labral reconstruction.

Known hip distraction devices are utilized while the patient is strapped to a surgical table to provide articulation of the hip joint. The articulation is accommodated through the use of a universal ball joint. The distraction can be performed using a mechanical external fixation device or with the use of an inflatable balloon. Another term for joint distraction is also known as arthrodiastasis.

While many external fixation devices have proven generally effective for stabilizing bones, these conventional systems are often difficult and time consuming to adjust once assembled, particularly since the surgeon may need to manually loosen and retighten the clamps attached to bone several times during the distraction process. Not only is the adjustment process time consuming, but the health and safety of the surgeon is also potentially compromised, particularly as the surgeon must expose his hands to the X-ray field during the reduction process.

Even more importantly, the healing process of the patient's health and rehabilitation can be compromised if the alignment of the bones, soft tissue or joints is not properly adjusted. For instance, known hip distractors can introduce a binding of the hinge located at the joint. While not completely understood, the probable causes of this binding force can include: 1) improper tolerances on the mating parts of the hinge joint; 2) off-axis loading causing the mating parts to rub, and from this friction, causing a binding force; or 3) improper alignment of the hinge joint with the rotation axis of the femoral head which limits rotation.

Consequently in view of the foregoing, what is needed is a joint distraction system which can be accurately adjusted to accommodate a wide variety of patients.

SUMMARY

According to one embodiment of the present disclosure there is provided an external fixation device for adjusting a load occurring at a joint connecting a first bone to a second bone. The device includes a first bone clamp configured to be attached to the first bone, a second bone clamp configured to be attached to the second bone, and a pivot assembly disposed between and operatively connected to the first bone clamp and to the second bone clamp. The pivot assembly defines a longitudinal axis and includes a first pivot body pivotably coupled to a second pivot body at a pivot axis, wherein one of the first pivot body and the second pivot body includes an adjustment mechanism configured to adjust the position of one of the first pivot body and the second pivot body with respect to the other of the first pivot body and the second pivot body at other than the pivot axis.

According another aspect of the present disclosure there is provided a method of adjusting a load occurring at a joint connecting a first bone to a second bone with an external fixation device having a first bone clamp configured to be attached to the first bone and a second bone clamp configured to be attached to the second bone. The method includes connecting the first bone clamp to the second bone clamp with a pivot assembly defining a longitudinal axis having a first pivot body pivotably coupled to a second pivot body at a hinge defining a pivot axis, moving the first pivot body with respect to the second pivot body about the hinge to a predetermined location, fixing the location of the first pivot body with respect to the second pivot body at the predetermined location, and adjusting the first pivot body with respect to the second pivot body along a direction inclined with respect to the longitudinal axis and inclined with respect to the pivot axis.

According to still another aspect of the present disclosure there is provided a pivot assembly defining a longitudinal axis and configured to adjust a load occurring at a joint disposed between a first bone, connected to a first bone clamp, and to a second bone, connected to a second bone clamp. The pivot assembly includes a first pivot body configured to be operatively connected to the first bone clamp and a second pivot body configured to be operatively connected to the second bone clamp. The second pivot body is pivotably coupled to the first pivot body at a hinge defining a pivot axis. One of the first pivot body and the second pivot body includes an adjustment mechanism configured to adjust the position of one of the first pivot body and the second pivot body with respect to the other of the first pivot body and the second pivot body along an adjustment axis inclined with respect to the longitudinal axis.

Other objects and benefits of the disclosure will become apparent from the following written description along with the accompanying figures.

DESCRIPTION

Figure 1:
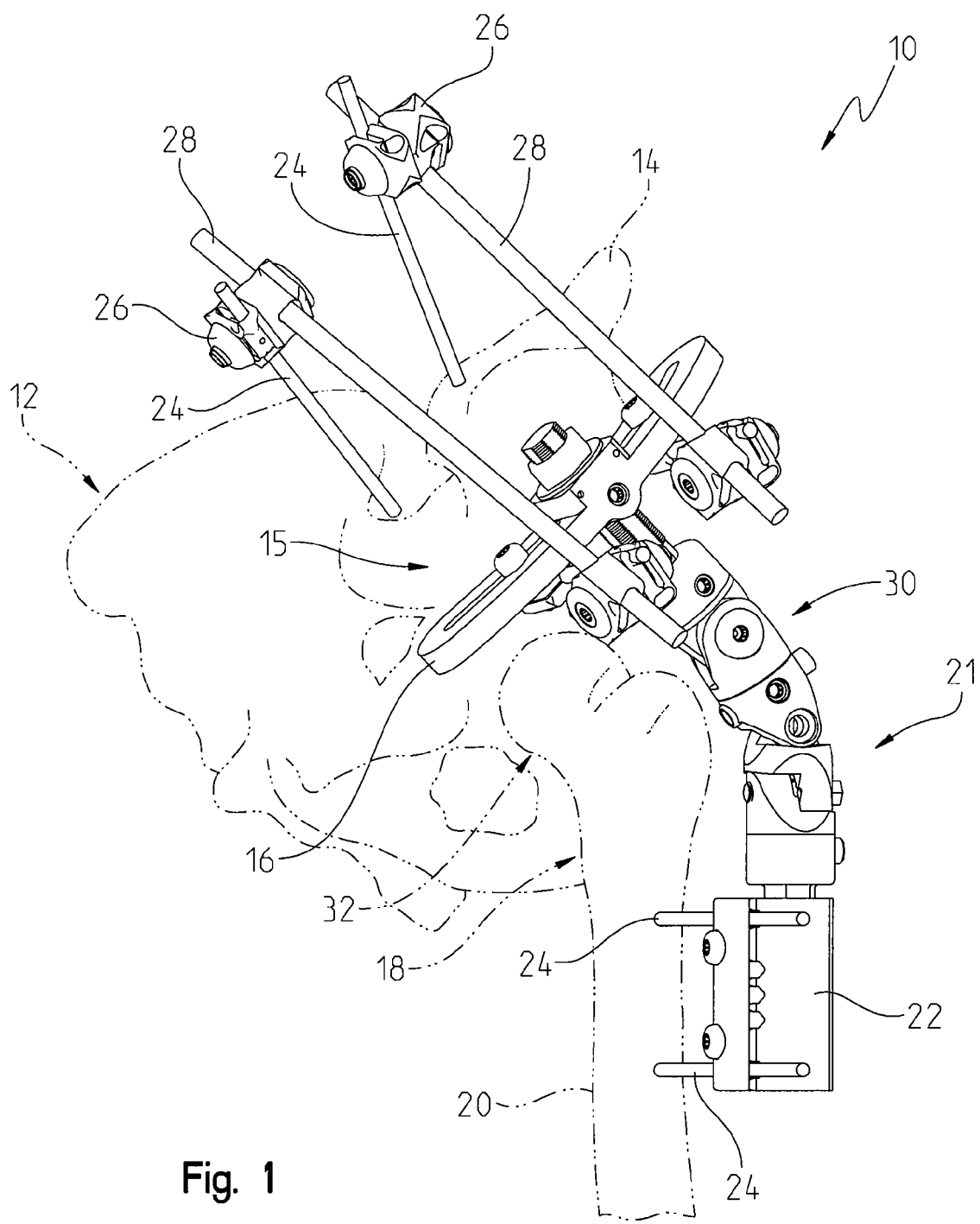
FIG. 1 is a perspective view of a joint distraction system configured to distract a hip joint.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles of the disclosure as would normally occur to one of ordinary skill in the art to which this disclosure pertains.

Unless defined otherwise, all technical and scientific terms used herein have the same meaning as commonly understood by one of ordinary skill in the art to which this application belongs. Although any method and materials similar or equivalent to those described herein can be used in the practice or testing of the present application, the specific methods and materials are now described.

Referring to FIG. 1, a joint distraction system 10, also known as an external fixation device, is configured to be connected to a hip bone 12, in particular the ilium 14, through a proximal assembly 15, including a hip distractor clamp 16, and to leg 18, in particular a femur 20, through distal assembly 21, including a fixator assembly 22 or a leg clamp. A left hip is illustrated. As can be seen in FIG. 1, the joint distraction system connects the hip bone 12, in particular the ilium, to a second bone, the femur 20, through a plurality of bone screws 24 as is understood by those skilled in the art. Bone screws 24 are coupled to the hip distractor clamp 16 through bone screw clamps 26 and extension rods 28.

Various components of the joint distraction system 10, which will be described in more detail below, including other components used therewith, such as attaching bone pins or wires (e.g., transfixing pins), and/or rods, bars, or other fixation devices (e.g., bone screws) as desirable for a particular fixation procedure are formed of many different types of materials. While not necessarily required, the described elements, in different embodiments, are radiographically translucent to enable viewing of a fracture/fusion site of the bones and joints on X-ray film or through digital radiography. The radiolucent components (or portions thereof) can be formed of, for example, carbon, composite, carbon fiber, or other radiolucent materials.

At the conclusion of a surgical procedure, the joint distraction system 10 is coupled to the hip bone 12 and to the leg bone 20. Once placement of the screws 24 at the hip bone 14 and the leg bone 20 has been selected, the length of the proximal assembly 15 and the distal assembly 21 are changed by adjusting the position of the location of the screws 24 and the extension rods 28 within the bone screw clamps 26. Adjustments are subsequently made to insure that the length of the proximal assembly 15 and the length of the fixator assembly 22 locate a pivot assembly 30 adjacent to a joint 32 connecting the hip to the leg.

While the adjustment of the overall length of the joint distraction system 10, including the placement of the bone screws 24 at the proper locations, provides for stabilization of the hip joint after a surgical procedure, the hip joint 32, in some instances, experiences a load which reduces the effectiveness of the healing processes. In some cases, bone deformities can complicate the placement of the joint distraction system 10, including the placement of the pivot assembly 30.

Figure 2:
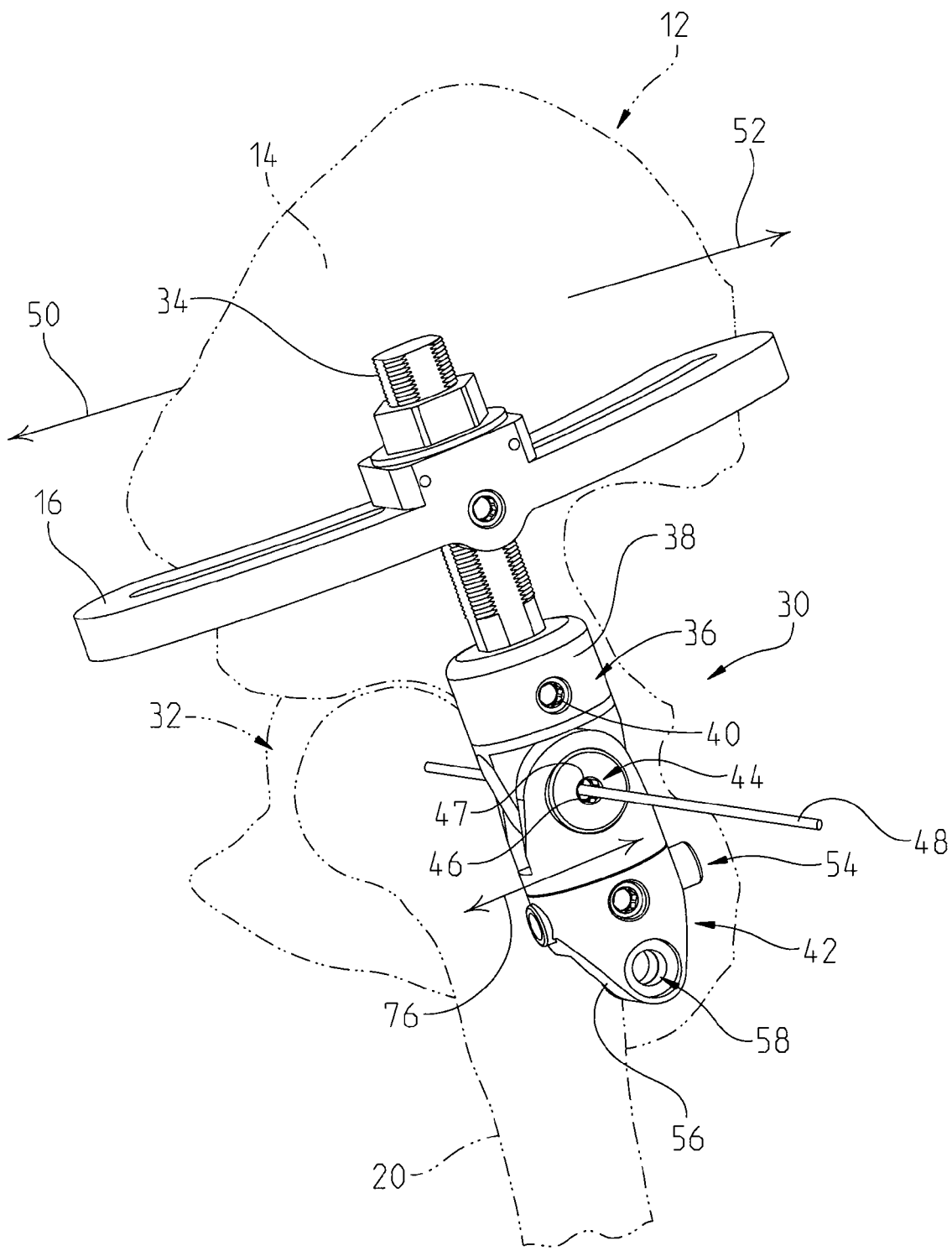
FIG. 2 is a perspective view of a hip distractor clamp and a pivot assembly coupled to the hip distractor clamp of FIG. 1.

As further illustrated in FIG. 2, the hip clamp 16 is coupled to the pivot assembly 30 with a distraction post 34 extending through the hip clamp 16 and operatively connected to a first pivot body 36 of the pivot assembly 30. The first pivot body 36 includes a head portion 38 into which the distraction post 34 is inserted. The head portion 38 includes an aperture to accommodate the insertion of a bolt 40, or other connector, which fixedly connects the first pivot body 36 to the clamp 16. In different embodiments, the bolt 50 includes a threaded cylinder.

The first pivot body 36 is pivotably coupled to a second pivot body 42 at a hinge 44 defining a pivot axis 46. The hinge 44 includes an aperture 47 through which a locating pin or screw 48 can be inserted. The locating screw 48 enables a user to properly locate the pivot axis 46 at the pivot axis of the joint 32. When properly aligned and properly located, the joint distraction system 10 is configured pivot about the pivot axis 46 which is defined along the axial length of the locating screw 48. Correct location of the pivot axis 46 with the hip joint 32 positions movement of the leg bone 20 with respect to the hip 12 at the hip joint 32.

The illustrated left hip bone 12 of FIG. 2 defines an anterior direction 50 generally defined as anterior to or in front of a plane extending laterally from one side, i.e. left, of a person to another side, i.e. right. A posterior direction 52 is defined as being posterior to or behind the same plane extending from one side of a person to another. To accommodate improved adjustability and a wider variety of disease conditions and patient shapes and sizes, the pivot assembly 30 includes an adjustment mechanism 54 configured to adjust a position of the joint distraction system 10 in both the anterior direction 50 and the posterior direction 52. The second pivot body 42 includes a boss 56 which extends from the second pivot body 42. The boss 56 defines an aperture 58 which is configured to couple to the distal assembly 21 of FIG. 1. Consequently, the joint distraction system is adjustable, in different embodiments, post-operatively in either one or both of the anterior or the posterior directions.

Figure 3:
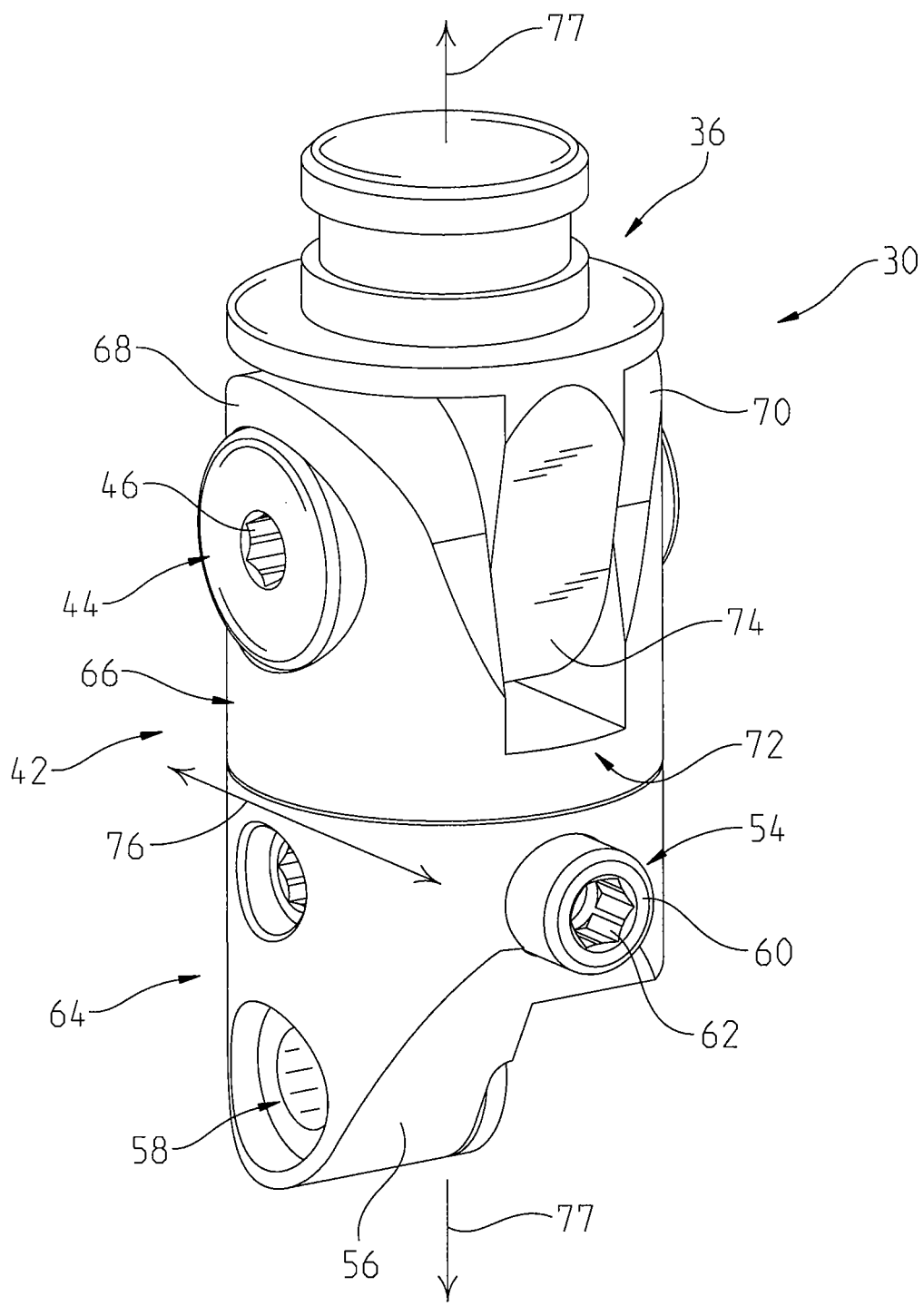
FIG. 3 is a perspective view of the pivot assembly of FIG. 2 including a first pivot body and a second pivot body.

FIG. 3 illustrates a perspective view of the pivot assembly 30 including the adjustment mechanism 54 and the boss 56. The adjustment assembly 54 includes a distraction nut 60, the configuration of which is more fully described in FIG. 4. The distraction nut 60 defines an aperture 62 configured to accept a tool (not shown) which is inserted into the aperture 62 and moved to rotate the distraction nut 60.

The second pivot body 42 includes a first part 64 which includes the boss 56 operatively connected to a second part 66 which defines the aperture 47 through which the locating pin or screw 48 is inserted. The second part 66 includes a first projection 68 and a second projection 70 coupled to and extending from a base 72. The first and second projections 68 and 70 are spaced apart to define a slot into which a portion 74 of the first pivot body 36 extends. The first projection 68, the second projection 70, and the portion 74 are configured to form the hinge 44.

Adjustment of the distraction nut 60 adjusts the location of one of the first part 64 and the second part 66 with respect to the other of the first part 64 and second part 66 linearly along a direction 76. The direction 76, which is also illustrated in FIG. 2, illustrates an adjustment direction of the distraction nut 62 in either the anterior direction 50 or the posterior direction 52. The direction 76 is substantially perpendicular to a longitudinal axis 77 defined by the pivot assembly 30 when the first pivot body 36 and the second pivot body 42 are aligned along the axis. The direction 76, also identified as an adjustment axis or adjustment direction, is therefore inclined with respect to the longitudinal axis 77. In the illustrated embodiment, the direction 76 is substantially perpendicular to the pivot axis 46 and to the longitudinal axis 77. The disclosed joint distraction system 10 is therefore configured in different embodiments to align the leg bone 20 with the hip bone 12 along the longitudinal direction of the femur, to align the leg bone 20 with the hip bone 12 about the pivot axis 46, and to align the leg bone 20 with the hip bone 12 in one of or both of the anterior and posterior directions. In this embodiment, the adjustment is made "below" the hinge 44, i.e. away from the hip bone and toward the end of leg bone. The adjustment procedure directed toward the end of the leg bone is also identified as a distal A-P (anterior-posterior) distraction.

Figure 4:
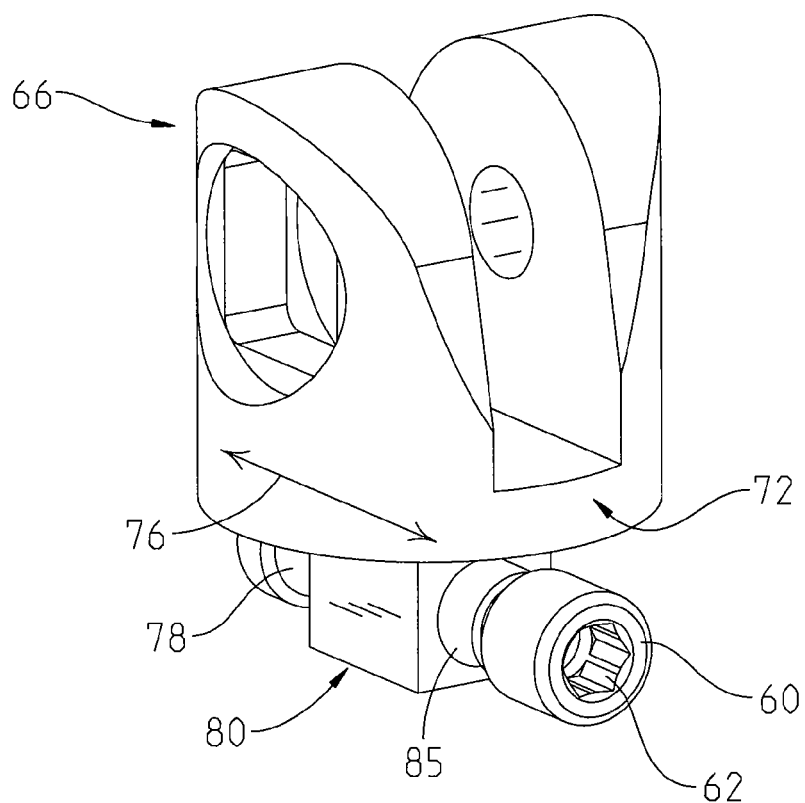
FIG. 4 is a second part of second pivot body of FIG. 3 including an adjustment mechanism.
Figure 5:
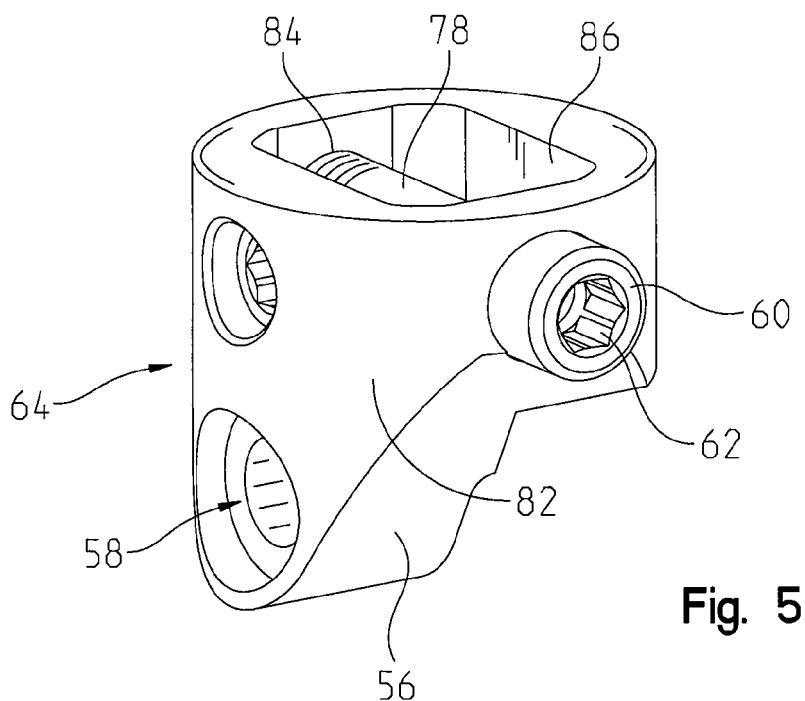
FIG. 5 is a first part of the second pivot body of FIG. 3 including the adjustment mechanism.

FIGS. 4 and 5 illustrate respectively the second part 66 and the first part 64. The distraction nut 60 and distraction bolt 78 are illustrated in each of the figures to show the location of the nut/bolt assembly with respect to each part, even though only one nut/bolt assembly is used in the second pivot body 42. When the first part 64 and second part 66 are coupled together, the bolt 78 extends through a wall 82 of the first part 64, through the cubular portion 80 of the second part 66 and through the wall 82 a second time at a location 84. The bolt 78 includes threads (not shown) which are configured to engage threads (also not shown) in the cubular portion 80. The cubular portion 80, in one embodiment, includes a sleeve 85 extending through the cubular portion 80 having the threads. In different embodiments, the sleeve 85 includes a hollow cylinder. The location of the bolt/nut is restricted by the wall 82 of the first part 64. When the cubular portion 80 is disposed within a cavity 86 of the first part 64, rotation of the bolt 78 about its longitudinal axis adjusts the position of the cubular portion 80 within the cavity 86. The position of the second part 66 is thereby moved with respect to the first part 64 to adjust the location of the distal assembly 21 in the anterior or posterior direction along the direction 76.

In one embodiment, the bolt 78 can be rotated with a five millimeter hex driver to allow up to four millimeters of distraction from center in either the anterior or posterior directions. The bolt 78 is therefore constrained positionally, but with rotation, provides motion due to the threads in the bolt and in the cubular portion 80.

Figure 6:
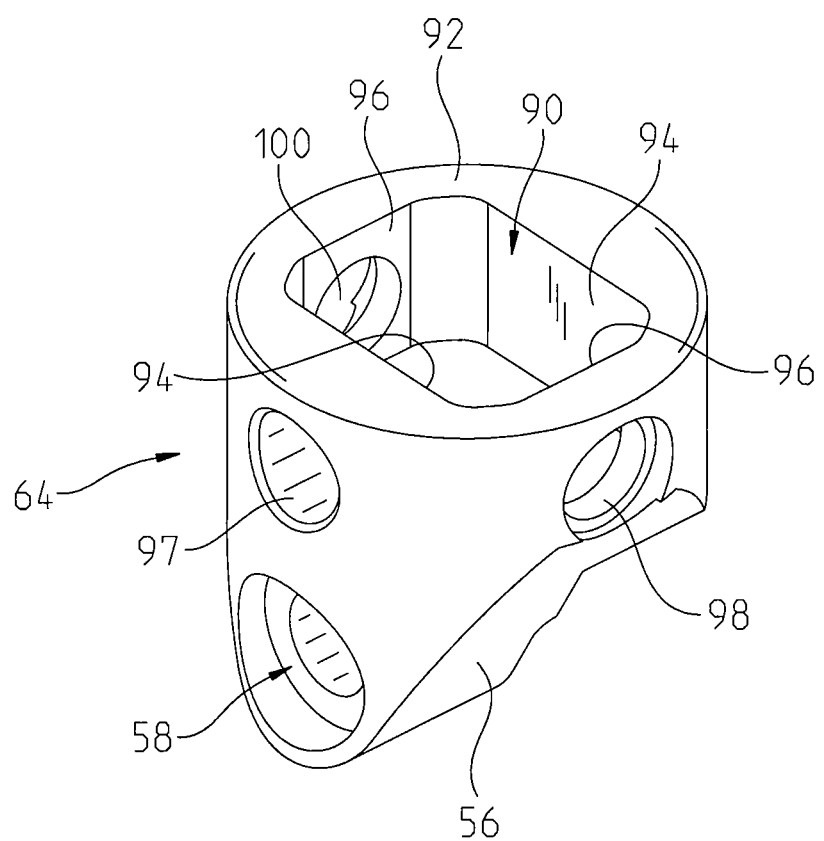
FIG. 6 is another embodiment of a first part of the second pivot body of FIG. 3 including the adjustment mechanism.

FIG. 6 illustrates another embodiment of the first part 64. In this embodiment, an aperture 90 is defined within a wall 92 of the first part 64. The wall 92 is configured to form a generally rectangular prism having a first pair of sidewalls 94 extending along the direction 76 and a second pair of sidewalls 96 generally perpendicular to the sidewalls 94. The cubular portion 80, which is located within the aperture 94, is configured such that sidewalls of the cubular portion 80 which are aligned along the same plane as the sidewalls 94 are sufficiently spaced apart from one another such that movement of the second part 66 along direction 76 is directed by the interface between the sidewalls 94 and the interfacing sidewalls of the cubular portion 80. The second part 66 is thereby restrained from becoming misaligned as the second portion 66 moves.

In other embodiments, the cubular portion 80 includes other configurations including a rectangular prism, a cuboid or a multi-sided extension from the base 72 having generally parallel sidewalls facing the sidewalls 94. FIG. 6 also illustrates apertures 98 and 100 through which the bolt 78 extends.

FIG. 6 further illustrates an aperture 97 through which a bolt (not shown) is inserted to fix or lock the position of the adjustment bolt 78 within the first part 64. The bolt acts as a limiter configured to limit movement of the adjustment bolt 78. An end of the bolt engages a side of the adjustment bolt to limit the rotation thereof. In this configuration, the limiter fixes the position of the adjustment bolt 78 to thereby lock the position of distraction assembly to prevent loss of hinge alignment.

Figure 7:
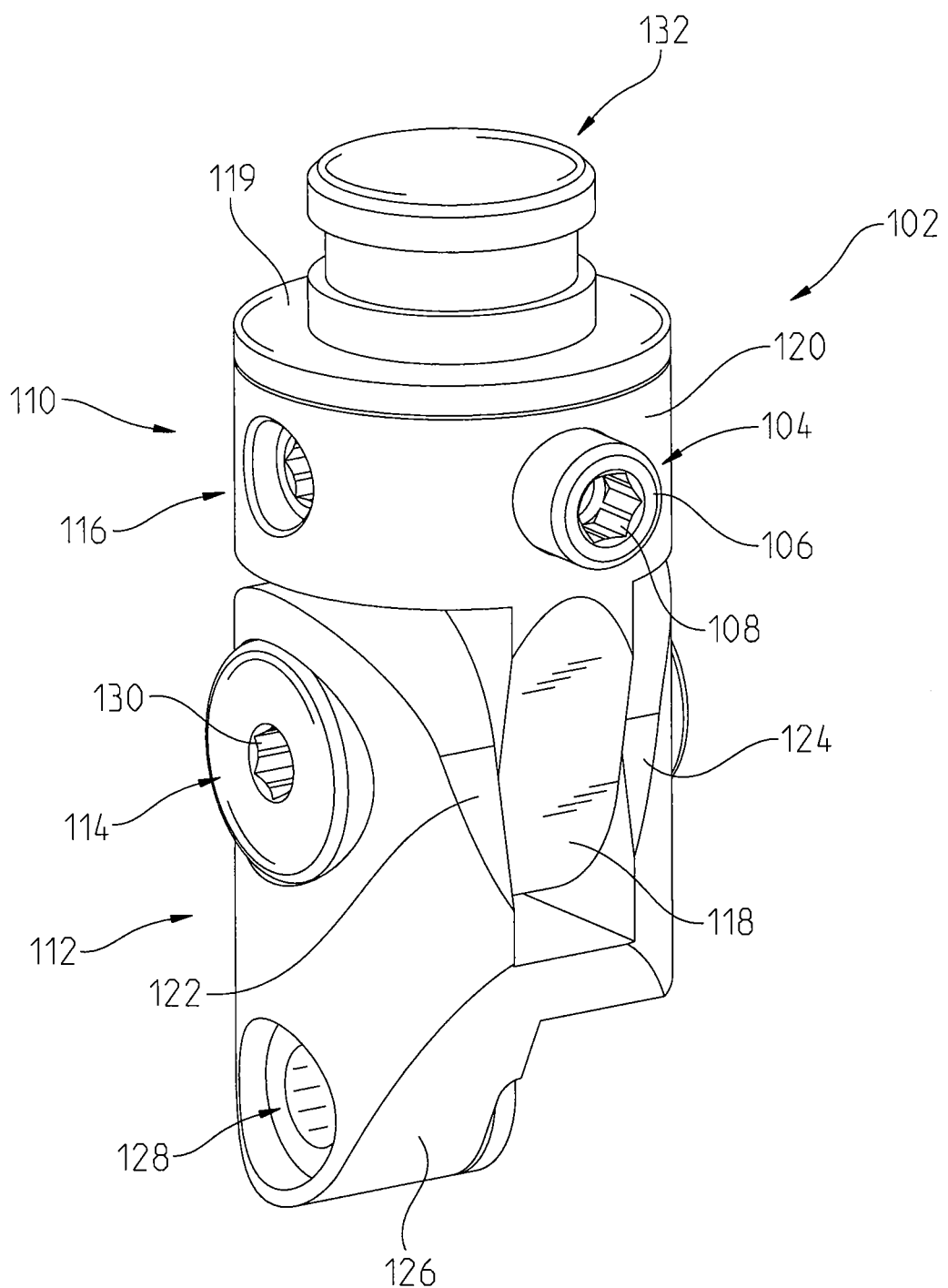
FIG. 7 is a perspective view of another embodiment of a pivot assembly including a first pivot body and a second pivot body.

FIG. 7 illustrates a perspective view of another embodiment of a pivot assembly identified as pivot assembly 102 including an adjustment assembly 104. The adjustment assembly 104 includes a distraction nut 106. The distraction nut 106 defines an aperture 108 configured to accept a tool (not shown) which is inserted into the aperture 108 as previously described. The pivot assembly 102 includes a first pivot body 110 operatively connected to a second pivot body 112 at a hinge 114.

The first pivot body 110 includes a first part 116, which includes a boss 118, and a second part 119. The boss 118 extends from a base portion 120 of the first part 116, and the adjustment assembly 104 extends therethrough. The boss 118 is located between first and second extending portions 122 and 124 of the second pivot body which cooperate to form the hinge 114. A boss 126 of the second pivot body 112 defines an aperture 128 configured to couple to the distal assembly 21 as previously described. The hinge 114 defines an aperture 130 configured to receive a locating pin or screw as described with respect to aperture 47. The first part 116 includes a connecting portion 132 configured to couple to proximal assembly 15. In this embodiment, the adjustment is made "above" the hinge 114, i.e. away from the end of the leg bone and toward the hip bone. The adjustment procedure directed toward the end of the hip bone is also identified as a proximal A-P distraction.

Figure 8:
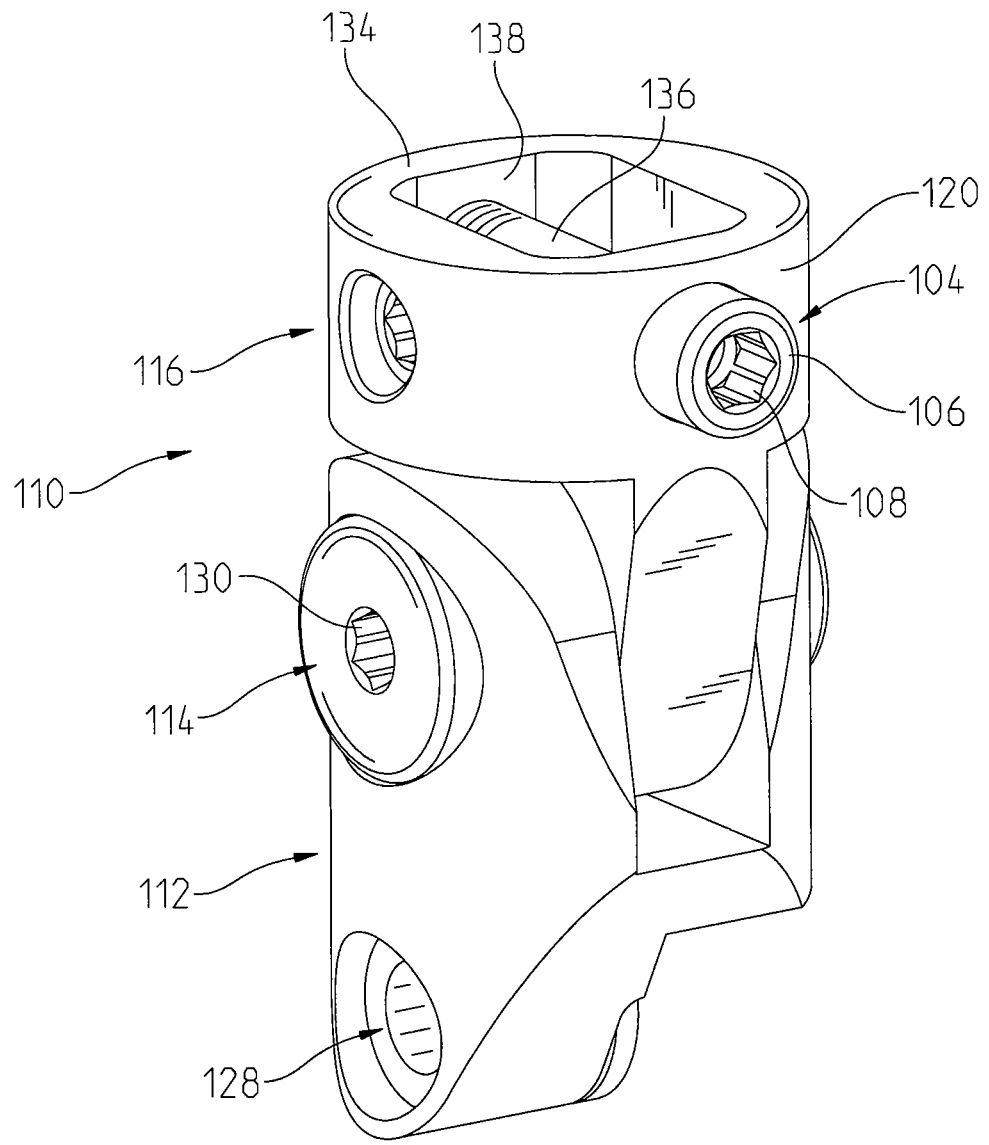
FIG. 8 is a perspective view of the pivot assembly of FIG. 7 illustrating a first part including a boss.

As further illustrated in FIG. 8, the first pivot body 110 is shown without the second part 119. The first part 116 includes a sidewall 134 having apertures through which an adjustment bolt 136 of the adjustment assembly 104 extends. The adjustment bolt 136 is longitudinally fixed within a cavity 138 defined by the sidewall 134. The adjustment bolt 136 is configured to rotate about the longitudinal axis thereof.

Figure 9:
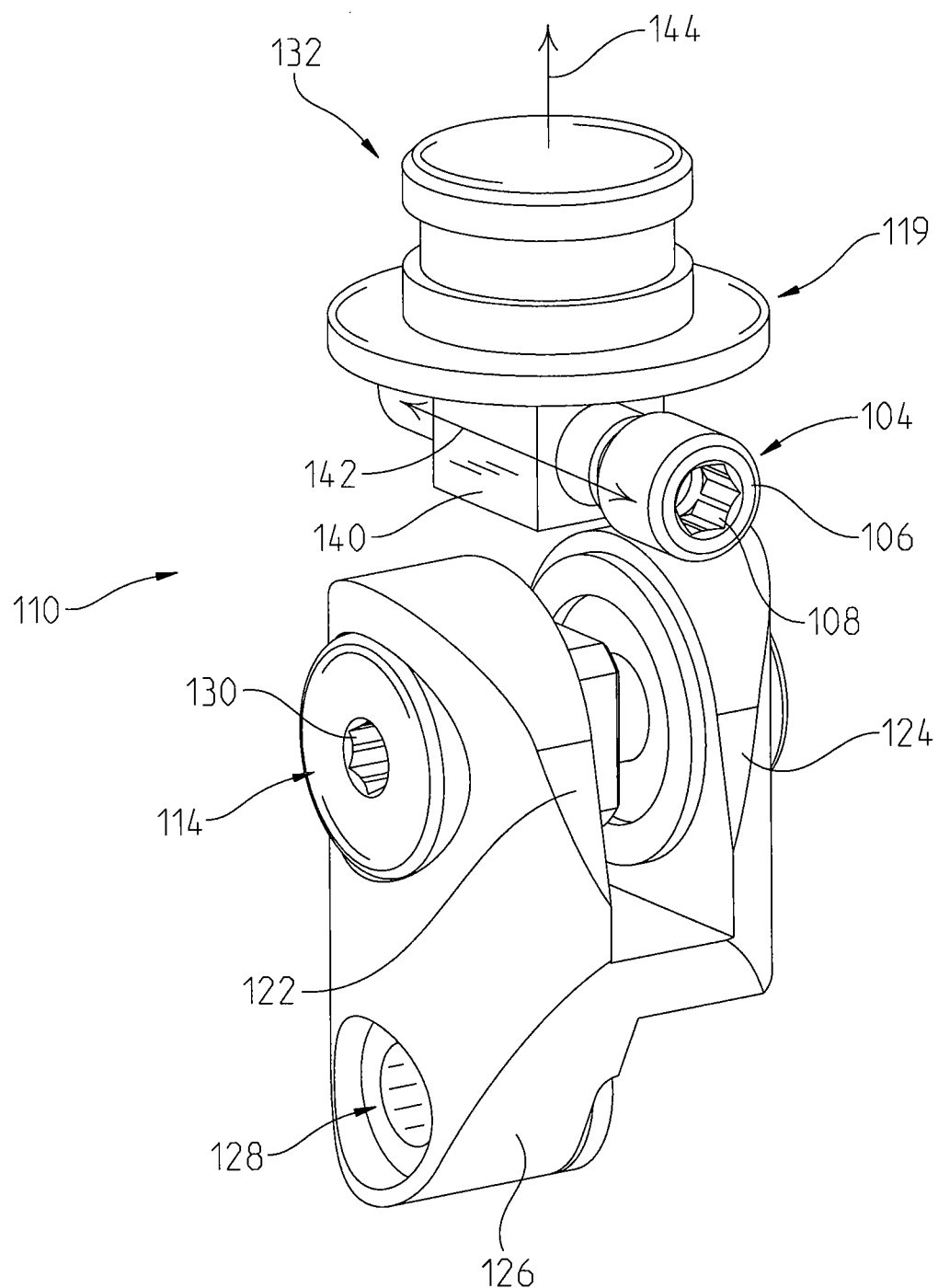
FIG. 9 is a perspective view of the pivot assembly of FIG. 7 illustrating a second part.

As can be seen in FIG. 9, which illustrates the second part 119 but does not illustrate the first part 116, the second part 119 includes a cubular portion 140 which is configured to be disposed within the cavity 138 of the first part 116. The cubular portion 140 includes a threaded aperture, in one embodiment, through which the adjustment bolt 136 threadingly engages the threaded aperture. Rotation of the adjustment bolt 136 moves the first part 116 and the second part 119 with respect to one another along the longitudinal axis of the threaded bolt to thereby displace one of the first part 116 and the second part 119 along an axis 142.

Figure 10:
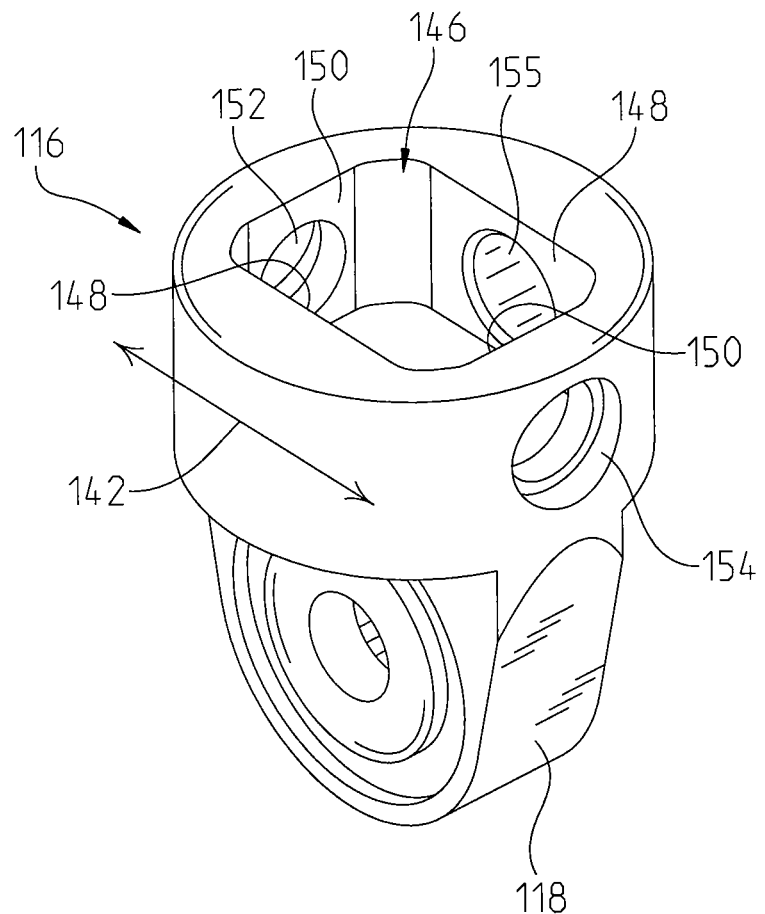
FIG. 10 is another embodiment of a first part of the first pivot body of FIG. 7.

FIG. 10 illustrates another embodiment of the first part 116 including the boss 118. The second part 116 includes the a cavity 146 defined by the base portion 120 to form a generally rectangular prism having a first pair of sidewalls 148 extending along the direction 142 and a second pair of sidewalls 150 extending generally perpendicular to the sidewalls 148. The cubular portion 140, which is located within the aperture cavity 146 in one embodiment, is configured such that sidewalls of the cubular portion 140 are aligned along the same plane as the sidewalls 148. The sidewalls of the cubular portion 140 are sufficiently spaced apart from one another such that movement of one of the first part 116 and second part 119 along direction 142 is directed by the interface between the sidewalls 148 and the interfacing sidewalls of the cubular portion 140. The first part 116 and the second part 119 are thereby restrained from becoming significantly misaligned within the cavity 146. In other embodiments, the cubular portion 140 includes other configurations including a rectangular prism, a cuboid or a multi-sided extension having generally parallel sidewalls facing the sidewalls 94. FIG. 10 also illustrates apertures 152 and 154 through which the adjustment bolt 136 extends.

FIG. 10 further illustrates an aperture 155 through which a bolt (not shown) is inserted to fix or lock the position of the adjustment bolt 136 within the first part 116. In this configuration, the fixed position of the adjustment bolt 136 thereby locks the position of distraction assembly to prevent loss of hinge alignment. The bolt acts as a limiter configured to limit movement of the adjustment bolt 136. In this configuration, the limiter fixes the position of the adjustment bolt 136 to thereby lock the position of the distraction assembly to prevent loss of hinge alignment.

Figure 11:
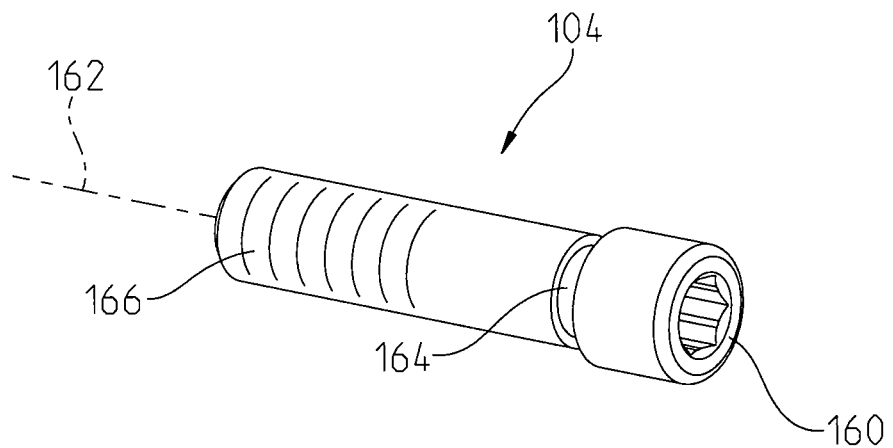
FIG. 11 is a perspective view of an adjustment mechanism configured to adjust the joint distraction system in an anterior or posterior direction.

FIG. 11 illustrates one embodiment of the adjustment mechanism 104 of FIG. 6. The adjustment assembly 104 includes a socket head 160 configured to engage a driver which is moved to rotate the socket head 160 about a longitudinal axis 162. The socket head 160 is coupled to a bolt 164, a portion of which is disposed within a sleeve 166. The bolt 164 includes threads configured to engage threads in the interior of the sleeve 166. The bolt 164, which is shown in FIG. 8, is located within the sleeve 166. The sleeve 166 is fixed with respect to the cubular portion 140 such that rotation of the bolt 164 moves the sleeve along the longitudinal direction 142. Since in one embodiment, the connecting portion 132 is fixed to the hip bone through the proximal assembly 15, the second pivot body 112 moves in the anterior or posterior direction as adjusted by a user.

In different embodiments, the adjustment mechanisms are adjusted with a 5 millimeter hex driver to allow up to 4 millimeter of distraction from center in either the anterior or posterior directions. In other embodiments, other sizes and types of driver are used to adjust system in the anterior or posterior directions in other distances of distraction. In still another embodiment, a maximum amount of distraction of 10 millimeters in either anterior or posterior directions is provided.

While an exemplary embodiment incorporating the principles of the present application has been disclosed hereinabove, the present application is not limited to the disclosed embodiments. Instead, this application is intended to cover any variations, uses, or adaptations of the application using its general principles. Further, this application is intended to cover such departures from the present disclosure as come within known or customary practice in the art to which this present application pertains and which fall within the limits of the appended claims.

The terminology used herein is for the purpose of describing particular illustrative embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations).

The invention claimed is:

1. An external fixation device for adjusting a load occurring at a joint connecting a first bone to a second bone, the device comprising:
    a first bone clamp configured to be attached to the first bone;
    a second bone clamp configured to be attached to the second bone; and
    a pivot assembly including a hinge having a pivot axis and defining an aperture, the aperture sized and shaped to receive a locating member configured to locate the pivot assembly adjacent the joint, the pivot assembly disposed between and operatively connected to the first bone clamp and to the second bone clamp, the pivot assembly defining a longitudinal axis and including a first pivot body pivotably coupled to a second pivot body at the hinge, wherein one of the first pivot body and the second pivot body includes an adjustment mechanism configured to adjust the position of one of the first pivot body and the second pivot body with respect to the other of the first pivot body and the second pivot body at other than the pivot axis.

2. The external fixation device of claim 1 wherein the pivot axis is substantially perpendicular to the longitudinal axis, and the adjustment mechanism defines an adjustment axis inclined with respect to the longitudinal axis, wherein the adjustment mechanism is configured to move one of the first pivot body and the second pivot body with respect to the other of the first pivot body and the second pivot body along the direction of the adjustment axis.

3. The external fixation device of claim 2 wherein the pivot assembly defines a proximal end on one side of the hinge and a distal end on another side of the hinge, wherein the adjustment axis is located between one of the proximal end and the hinge and the other of the distal end and the hinge.

4. The external fixation device of claim 3 wherein one of the first pivot body and one of the second pivot body comprises a first part and a second part wherein the adjustment mechanism is configured to move the first part with respect to the second part along the adjustment axis.

5. The external fixation device of claim 4 wherein the adjustment axis is substantially perpendicular to the pivot axis and substantially perpendicular to the longitudinal axis.

6. The external fixation device of claim 4 wherein the adjustment mechanism comprises a geared assembly.

7. The external fixation device of claim 6 wherein the geared assembly comprises a threaded aperture and a threaded cylinder configured to threadingly engage the threaded aperture.

8. The external fixation device of claim 7 wherein the threaded cylinder is located in one of the first part and the second part such that rotational movement of the threaded cylinder is configured to adjust the position of the first part with respect to the second part along the adjustment axis.

9. The external fixation device of claim 8 further comprising a retaining member configured to retain the position of the first pivot body with respect to the second pivot body about the pivot axis.

10. The external fixation device of claim 7 wherein the threaded aperture is located between the proximal end and the hinge.

11. The external fixation device of claim 7 wherein the threaded aperture is located between the distal end and the hinge.

12. A method of adjusting a load occurring at a joint connecting a first bone to a second bone with an external fixation device having a first bone clamp configured to be attached to the first bone and a second bone clamp configured to be attached to the second bone, the method comprising:
    connecting the first bone clamp to the second bone clamp with a pivot assembly defining a longitudinal axis having a first pivot body pivotably coupled to a second pivot body at a hinge defining a pivot axis and defining an aperture, the aperture sized and shaped to receive a locating member configured to locate the pivot assembly adjacent the joint;
    moving the first pivot body with respect to the second pivot body about the hinge to a predetermined location;
    inserting the locating member through the aperture to locate the pivot assembly adjacent the joint;
    fixing the location of the first pivot body with respect to the second pivot body at the predetermined location;
    adjusting the first pivot body with respect to the second pivot body along a direction inclined with respect to the longitudinal axis and inclined with respect to the pivot axis.

13. The method of claim 12 wherein the adjusting the first pivot body with respect to the second pivot body includes adjusting the first pivot body with respect to the second pivot body along a direction substantially perpendicular to the pivot axis.

14. The method of claim 13 wherein the adjusting the first pivot body with respect to the second pivot body includes rotating a geared assembly about the direction substantially perpendicular to the pivot axis.

15. A pivot assembly defining a longitudinal axis and configured to adjust a load occurring at a joint disposed between a first bone, connected to a first bone clamp, and to a second bone, connected to a second bone clamp, the pivot assembly comprising:
    a first pivot body configured to be operatively connected to the first bone clamp;
    a second pivot body configured to be operatively connected to the second bone clamp, the second pivot body pivotably coupled to the first pivot body at a hinge defining a pivot axis and defining an aperture, the aperture sized and shaped to receive a locating member configured to locate the pivot assembly adjacent the joint,
    wherein one of the first pivot body and the second pivot body includes an adjustment mechanism configured to adjust the position of one of the first pivot body and the second pivot body with respect to the other of the first pivot body and the second pivot body along an adjustment axis inclined with respect to the longitudinal axis.

16. The pivot assembly of claim 15 wherein the adjustment mechanism comprises a geared assembly.

17. The pivot assembly of claim 16 wherein the geared assembly comprises a threaded aperture and a threaded cylinder configured to threadingly engage the threaded aperture.

18. The pivot assembly of claim 17 wherein the threaded cylinder is located in one of the first part and the second part such that rotational movement of the threaded cylinder adjusts the position of the first part with respect to the second part along the adjustment axis.

19. The pivot assembly of claim 18 wherein the pivot assembly defines a proximal end along the longitudinal axis on one side of the hinge and a distal end along the longitudinal axis on another side of the hinge, wherein the adjustment axis is located between one of the proximal end and the hinge and the other of the distal end and the hinge.

20. The pivot assembly of claim 18 wherein one of the first pivot body and one of the second pivot body comprises a first part and a second part and the adjustment mechanism is configured to move the first part with respect to the second part along the adjustment axis.

21. The pivot assembly of claim 20 wherein one of the first part and the second part includes a limiter configured to limit movement of the adjustment mechanism.

* * * * *